(12) United States Patent
Falco et al.

(10) Patent No.: US 7,470,814 B1
(45) Date of Patent: Dec. 30, 2008

(54) PROCESS FOR THE PREPARATION OF SUBSTITUTED 7-ALLYL-6-HYDROXY-INDANES

(75) Inventors: Josep Lluis Falco, Barcelona (ES); Albert Palomer, Barcelona (ES); Antonio Guglietta, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 0 days.

(21) Appl. No.: 11/980,816

(22) Filed: Oct. 31, 2007

(51) Int. Cl.
  *C07C 231/12* (2006.01)
(52) U.S. Cl. ............................................ 564/219
(58) Field of Classification Search .................. None
  See application file for complete search history.

(56) References Cited

U.S. PATENT DOCUMENTS 6,034,239 A * 3/2000 Ohkawa et al. ............. 544/147
6,218,429 B1 * 4/2001 Ohkawa et al. ............. 514/468

OTHER PUBLICATIONS

Uchikawa et al., J. Med. Chem. (2002), 45(19), p. 4222-4239.*

* cited by examiner

*Primary Examiner*—Brian J Davis
(74) *Attorney, Agent, or Firm*—Birch, Stewart, Kolasch & Birch, LLP

(57) ABSTRACT

The present invention relates to a novel process for the industrial manufacture of substituted 7-allyl-6-hydroxy-indanes of formula (I)

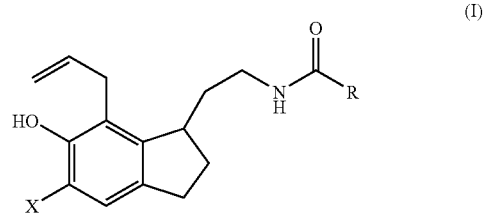

wherein R is a straight or branched ($C_1$-$C_6$)alkyl group and X is a halogen and enantiomers thereof.

13 Claims, No Drawings

PROCESS FOR THE PREPARATION OF SUBSTITUTED 7-ALLYL-6-HYDROXY-INDANES

FIELD OF THE INVENTION

The present invention relates to a novel process for the preparation of substituted 7-allyl-6-hydroxy-indanes of formula (I)

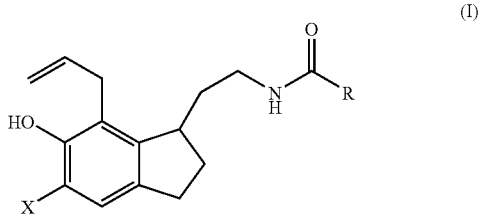

(I)

wherein R is a straight or branched ($C_1$-$C_6$)alkyl group and X is a halogen selected from the group consisting of F, Cl, Br, and I; and enantiomers thereof.

BACKGROUND OF THE INVENTION

The compounds of formula (I) belong to a known class of compounds related to melatonin agonists. For instance, the substituted 7-allyl-6-hydroxy-indanes of formula (I) wherein R is ethyl and X is bromine, and its (S)-enantiomer, are key intermediates in the process for the preparation of ramelteon, N-[2-[(8S)-1,6,7,8-tetrahydro-2H-indene[5,4-b]furan-8-yl]ethyl]-propionamide, a well known melatonin agonist, and have been prepared from the corresponding substituted 6-allyloxy-indanes (II) by rearrangement of allyl group in N,N-diethylaniline for 2.5 hours at 200-205° C. under argon atmosphere in a 80% yield (U.S. Pat. No. 6,034,239; U.S. Pat. No. 6,218,429; and Uchikawa et al., J. Med. Chem. 2002, 45, 4222-4239). Furthermore, WO 2007109141 discloses fluoro analogs of ramelteon which can be obtained from the corresponding 7-allyl-6-hydroxy-indanes of formula (I) wherein R is ethyl or propyl, and X is fluorine, which in turn are prepared from appropriate intermediates (II) by the same process.

SUMMARY OF THE INVENTION

In accordance with the present invention it has been found that the compounds of formula (I) can be conveniently prepared by exposing the corresponding substituted 6-allyloxy-indanes of formula (II)

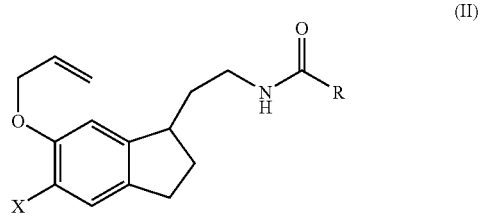

(II)

wherein R and X are as above, under the influence of microwaves in a polar solvent, while the stereochemistry on the carbon atom at position 1 in the indane ring is retained.

DETAILED DESCRIPTION OF THE INVENTION

The process of the present invention proceeds in higher yields and in shorter reaction time than the prior art methods, providing the desired products with a yield higher than 90% in a few minutes. Furthermore the present process has the advantage that inert atmosphere is not needed.

The term "microwave" as used herein refers to the region of the electromagnetic spectrum having power rating ranges of about 100W to about 400 W. In a preferred embodiment of the invention, a microwave source refers particularly to such power ratings, specifically from 100(±10) W to 400(±10) W. In a more preferred embodiment a microwave source of 300 (±10) W is used.

As used herein "polar solvent" means a solvent which has a dielectric constant of 6 debyes (25° C.) or greater. In a preferred embodiment of the invention, the solvents are selected from acetic acid, acetone, acetonitrile, dimethylacetamide, dimethylformamide, dimethyl sulfoxide, dioxane, ethanol, ethyl acetate, formic acid, hexamethylphosphoramide, i-propanol, methanol, t-butanol, tetrahydrofuran, and the like, and mixtures thereof. In a more preferred embodiment dimethylformamide is selected.

The reaction proceeds rapidly in a sealed vessel at a temperature ranging about 100 to about 250° C. In a preferred embodiment the temperature ranges from 220 to 240° C.

In a preferred embodiment, R is ethyl. However, any compound of general formula (I) wherein R is lower alkyl can be prepared by the process of the present invention. The term lower alkyl as used herein denotes a straight or branched alkyl chain groups having up to 6 carbon atoms, such as methyl, ethyl, propyl, i-propyl, n-butyl, s-butyl, t-butyl, n-pentyl, n-hexyl and isomers thereof.

In a preferred embodiment, X is selected from F and Br.

In a preferred embodiment, the compound of formula (I) is N-[2-(7-allyl-5-bromo-6-hydroxy-indan-1-yl)-ethyl]-propionamide and the compound of formula (II) is N-[2-(6-allyloxy-5-bromo-indan-1-yl)-ethyl]-propionamide.

In another preferred embodiment, the compound of formula (I) is (S)—N-[2-(7-allyl-5-bromo-6-hydroxy-indan-1-yl)-ethyl]-propionamide and the compound of formula (II) is (S)—N-[2-(6-allyloxy-5-bromo-indan-1-yl)-ethyl]-propionamide.

In a preferred embodiment, the compound of formula (I) is N-[2-(7-allyl-5-fluoro-6-hydroxy-indan-1-yl)-ethyl]-propionamide and the compound of formula (II) is N-[2-(6-allyloxy-5-fluoro-indan-1-yl)-ethyl]-propionamide.

In another preferred embodiment, the compound of formula (I) is (S)—N-[2-(7-allyl-5-fluoro-6-hydroxy-indan-1-yl)-ethyl]-propionamide and the compound of formula (II) is (S)—N-[2-(6-allyloxy-5-fluoro-indan-1-yl)-ethyl]-propionamide.

Intermediate compounds (II) in the present invention can be obtained according to U.S. Pat. No. 6,034,239, U.S. Pat. No. 6,218,429, and Uchikawa et al., J. Med. Chem. 2002, 45, 4222-4239.

When the reaction is complete, the products obtained can be isolated from the reaction mixture by any process well known to people skilled in the art. When the polar solvent used is dimethylformamide, the final products can be easily isolated from the reaction mixture by evaporation. Furthermore the present process has the advantage that dimethylformamide is a better solvent than those used in the prior art in terms of evaporation, such as N,N-diethylaniline.

Having described this invention in general terms, a further understanding can be obtained by referring to a specific example which is provided herein for illustration purposes only and is not intended to be limiting unless otherwise specified.

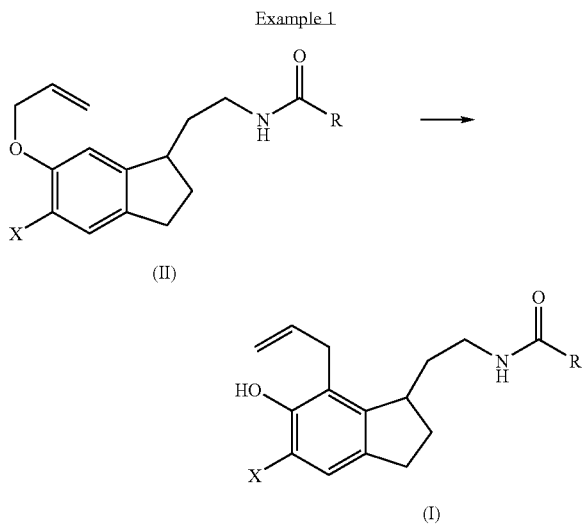

A solution of N-[2-(6-allyloxy-5-bromo-indan-1-yl)-ethyl]-propionamide (II, R=C$_2$H$_5$, X=Br) (2.39 g, 6.78 mmol) in 17 mL of anhydrous dimethylformamide are placed in a sealed vial and irradiated under microwaves (300 w, 5 min, 230° C.). The resulting solution is allowed to cool and 50 mL of water are added. The mixture is extracted with 3×30 mL of ethyl acetate, and the combined organic extractes are washed with water. The resulting organic phase is dried over magnesium sulphate, filtered, and the solvent is removed in vacuo, to yield 2.3 g of N-[2-(7-allyl-5-bromo-6-hydroxy-indan-1-yl)-ethyl]-propionamide (I, R=C$_2$H$_5$, X=Br) (yield 91%) as a yellowish solid. Purity: 95%. LCMS: 353 (M+1).

The invention claimed is:

1. A process for the preparation of compounds of formula (I)

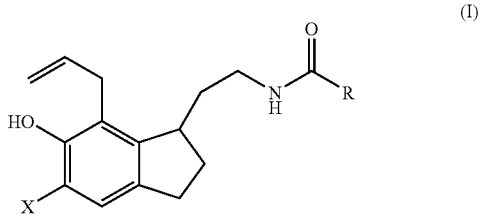

wherein R is a straight or branched (C$_1$-C$_6$)alkyl group and X is a halogen selected from the group consisting of F, Cl, Br, and I; and
enantiomers thereof,
which comprises exposing a compound of formula (II)

wherein R and X are as above,
under the influence of microwaves in a polar solvent which has a dielectric constant of 6 debyes or greater, when measured at 25° C., said process retaining the stereochemical integrity of the carbon at position 1 in the indane ring.

2. A process of claim 1, wherein a microwave source of 100(±10) W to 400(±10) W is used.

3. A process of claim 2, wherein a microwave source of 300(±10) W is used.

4. A process of claim 1, which is performed at a temperature from 100 to 250° C.

5. A process of claim 4, which is performed at a temperature from 220 to 240° C.

6. A process of claim 1, wherein the solvent is selected from acetic acid, acetone, acetonitrile, dimethylacetamide, dimethylformamide, dimethyl sulfoxide, dioxane, ethanol, ethyl acetate, formic acid, hexamethylphosphoramide, i-propanol, methanol, t-butanol, tetrahydrofuran, and water, and mixtures thereof.

7. A process of claim 6, wherein the solvent is dimethylformamide.

8. A process of claim 1, wherein in the compounds of formula (I) and (II), R is ethyl.

9. A process of claim 1, wherein in the compounds of formula (I) and (II), X is selected from the group consisting of F and Br.

10. A process of claim 1, wherein the compound of formula (I) is N-[2-(7-allyl-5-bromo-6-hydroxy-indan-1-yl)-ethyl]-propionamide and the compound of formula (II) is N-[2-(6-allyloxy-5-bromo-indan-1-yl)-ethyl]-propionamide.

11. A process of claim 1, wherein the compound of formula (I) is (S)—N-[2-(7-allyl-5-bromo-6-hydroxy-indan-1-yl)-ethyl]-propionamide and the compound of formula (II) is (S)—N-[2-(6-allyloxy-5-bromo-indan-1-yl)-ethyl]-propionamide.

12. A process of claim 1, wherein the compound of formula (I) is N-[2-(7-allyl-5-fluoro-6-hydroxy-indan-1-yl)-ethyl]-propionamide and the compound of formula (II) is N-[2-(6-allyloxy-5-fluoro-indan-1-yl)-ethyl]-propionamide.

13. A process of claim 1, wherein the compound of formula (I) is (S)—N-[2-(7-allyl-5-fluoro-6-hydroxy-indan-1-yl)-ethyl]-propionamide and the compound of formula (II) is (S)—N-[2-(6-allyloxy-5-fluoro-indan-1-yl)-ethyl]-propionamide.

* * * * *